(12) United States Patent
Yilmaz et al.

(10) Patent No.: US 9,980,931 B2
(45) Date of Patent: May 29, 2018

(54) USE OF GLYCYL GLUTAMINE AGAINST DEPRESSION

(71) Applicants: ULUDAG UNIVERSITESI TEKNOLOJI TRANSFER OFISI TICARET VE SANAYI ANONIM SIRKETI, Nilufer, Bursa (TR); Mustafa Sertaç Yilmaz, Bursa (TR); Sinan Ç avun, Bursa (TR)

(72) Inventors: Mustafa Sertaç Yilmaz, Bursa (TR); Sinan Ç avun, Bursa (TR)

(73) Assignees: Uludag Universitesi Teknoloji Transfer Ofisi Ticaret Ve Sanayi Anonim Suirketi, Bursa (TR); Mustafa Sertac Yilmaz, Bursa (TR); Sinan Cavub, Bursa (TR)

( * ) Notice: Subject to any disclaimer, the term of this patent is extended or adjusted under 35 U.S.C. 154(b) by 0 days. days.

(21) Appl. No.: 14/760,431

(22) PCT Filed: Jan. 10, 2014

(86) PCT No.: PCT/TR2014/000005
§ 371 (c)(1),
(2) Date: Jul. 10, 2015

(87) PCT Pub. No.: WO2014/109725
PCT Pub. Date: Jul. 17, 2014

(65) Prior Publication Data
US 2015/0352174 A1     Dec. 10, 2015

(30) Foreign Application Priority Data

Jan. 11, 2013   (TR) .................................. 2013/00427
Jan. 10, 2014   (TR) .................................. 2014/00278

(51) Int. Cl.
| | | |
|---|---|---|
| A01K 31/00 | (2006.01) |
| A61K 31/195 | (2006.01) |
| A61K 45/06 | (2006.01) |
| A61K 38/05 | (2006.01) |
| A61K 31/00 | (2006.01) |

(52) U.S. Cl.
CPC ............ *A61K 31/195* (2013.01); *A61K 31/00* (2013.01); *A61K 38/05* (2013.01); *A61K 45/06* (2013.01)

(58) Field of Classification Search
None
See application file for complete search history.

(56) References Cited

U.S. PATENT DOCUMENTS

2010/0016207 A1*   1/2010   Wurtman .............. A61K 38/16
                                                                  514/1.1

FOREIGN PATENT DOCUMENTS

WO   2007059031 A2   5/2007

OTHER PUBLICATIONS

Cavun et al., J. Pharm. Exp. Therap., 2005, 315(2):949-58.*
International Search Report for corresponding International Application No. PCT/TR2014/000005.
Langer K: "Development of an intravenous glutamine supply through dipeptide technology.", Nutrition (Burbank, Los Angeles County, Calif.) Nov.-Dec. 1996, vol. 12, No. 11-12 Suppl, Nov. 1996 (Nov. 1996), pp. S76-S77.
Yong Zhang et al: "Original Article Effects of glycyl-glutamine dipeptide supplementation on myocardial damage and cardiac function in rats after severe burn injury", Int J Clin Exp Pathol, vol. 6, No. 5, Jan. 1, 2013 (Jan. 1, 2013) , pp. 821-830.
M R Caira et al: "Crystal structure of the dipeptide cyclo(glycyl-L-glutamine)", Analytical Sciences, vol. 18, No. 10, Jan. 1, 2002 (Jan. 1, 2002), pp. 1175-1176.

* cited by examiner

*Primary Examiner* — Olga N Chernyshev
(74) *Attorney, Agent, or Firm* — Egbert Law Offices, PLLC

(57) ABSTRACT

A prophylactic or therapeutic agent is provided for depression (including each subtype according to DSM-IV of depression) or anxiety by increasing the levels of serotonin in the brain includes administration of glycyl-glutamine or cyclo glycyl-glutamine, a derivative that could cross the blood-brain barrier and could be used in peripheral applications.

8 Claims, 4 Drawing Sheets

USE OF GLYCYL GLUTAMINE AGAINST DEPRESSION

TECHNICAL FIELD

Figure 1:
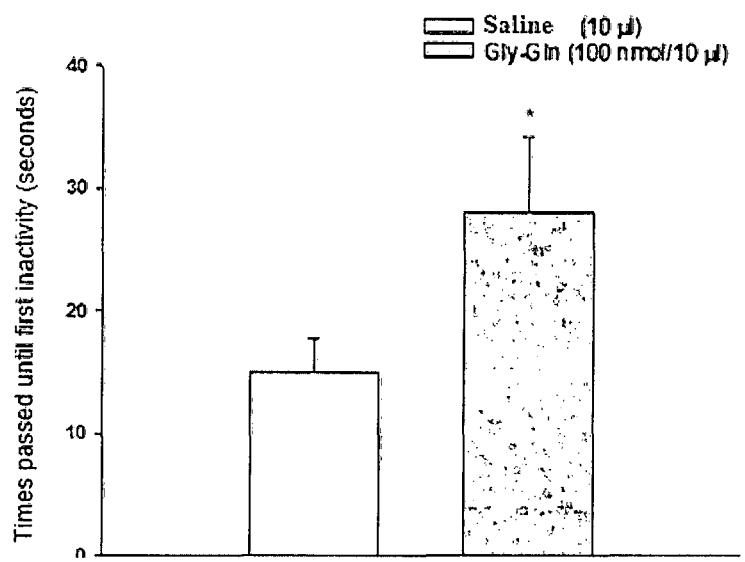

This invention is about, the glycyl-glutamine molecule; a molecule can be synthesized also in our body endogenously, which is extremely safe with its adverse effects.

This invention is particularly about use of glycyl-glutamine molecule administration in the treatment and/or prophylaxis of clinical conditions such as depression (bipolar depression, major depression, etc.) and anxiety disorders (anxiety, fear, stress and pressure) via increasing serotonin levels in the brain.

PRIOR ART

Depression and anxiety are the most common psychiatric disorders all around the world and its prevalence in developing countries at high levels as 21%. The treatment of depression and anxiety is of a great importance because they shall be one of the disorders, which shall extensively influence the World in the future. Various antidepressants are used for treating people developed depression and anxiety.

The term of depression does not describe a particular disorder, however it means a group of disorders, which occurs various subtypes. There are various systems for classifying mental disorders. Currently most widely accepted classifying system is DSM-IV (Diagnostic and Statistical Manual of Mental Disorders, Fourth Edition) which is a publication of The American Psychological Association (APA).

Subtypes of depression according to DSM-IV:
1. Major depressive disorder
2. Dysthymic disorder
3. Depression in bipolar disorder
4. Depression due to a general medical condition
5. Adjustment disorder with depressed mood
6. Depressive disorder not otherwise specified
   a. Premenstrual dysphoric disorder
   b. Minor depressive Disorder
   c. Recurrent brief depressive disorder As used herein, the term 'depression' refers to the disorders all of the mentioned above. It is already shown that the defects on serotonergic functionality play a role in the etiopathology of depression and anxiety. Due to serotonergic deficit; depression, anxiety, panic, phobias, obsessions and compulsions might occur. The most important serotonergic receptors for depression and anxiety are 5-HT1A, 5-HT1C and 5-HT2 (Baldwin and Rudge 1995, Lesch 1991, Stahl 2000). Thus, selective serotonin reuptake inhibitors (SSRI) are widely in use for the treatment of depression: However, these drugs have several side effects such as uneasiness, motor dysfunction, sexual dysfunction and diarrhea.

Despite the developing knowledge on depression pathophysiology and impact mechanisms of antidepressants, the preclinical studies performed on that field still maintain their importance even gradually increases due to clinical problems such as not being able to receive high positive results and receiving delayed results. The high rate of patients who still have not responded to treatment makes it necessary to continue to search newer, stronger and faster treatment approaches on that field. The current medications used in depression treatment are also very troublesome drugs in respect of adverse effects they cause. Today, the risks and adverse effects of antidepressants used for depression treatment spread in a large range from sexual problems to drug addiction and increasing suicidal tendency among young people.

Briefly, in current depression treatment;
There are patients, who cannot get any response,
Adverse effect potential of current drugs is high,
Response term is very long.

As a result, due to negative issues stated above and insufficiency of current solutions on the issue, it has been made mandatory to make technical developments related with improving and treating the people with depression and anxiety disorders.

PURPOSE OF THE INVENTION

This innovation is related with the use of glycyl-glutamine in the treatment and/or prophylaxis of depression disorder and/or anxiety, which meets all above-mentioned requirements, eliminates all disadvantages and provides some advantages. The purpose of the current invention is to use Glycyl-Glutamine (Gly-Gln) in the treatment and/or prophylaxis of depression and/or anxiety via its effects in the brain other than its metabolic products' (glycine and glutamine) separate effects. Previous reports already showed that Gly-Gln has different effects than its hydrolysis products (Unal et al., 1997). Hence these results exert that mechanisms of Gly-Gln's antidepressant effects are distinct than its hydrolysis products glutamine, which its antidepressant effects protected by a patent (WO 2007/059031). Glutamine exerts antidepressant effects by increasing gamma-aminobutyric acid (GABA) in the brain however Gly-Gln generates antidepressant effects by increasing serotonin levels in the brain. As a matter of fact, data from our laboratory showed that Gly-Gln administration does not alter GABA levels in the brain. Although glutamine administration increases GABA levels in the brain.

In a previous report it is already shown that Gly-Gln has beneficial effects on myocardial damage after severe burn injury (Zhang et al., 2013). However there is no report in the literature about Gly-Gln's beneficial effects against depression and/or anxiety and its use in the treatment and/or prophylaxis in depression and/or anxiety.

The primary purpose of the invention is to use Glycyl-Glutamine (Gly-Gln), as a molecule which can be synthesized in our body endogenously and use that molecule in the treatment and/or prophylaxis of depression and anxiety disorder by increasing serotonin levels which decreasing during those disorders. Above mentioned Gly-Gln is important because it can be endogenously synthesized in the body and exist during normal operation of it.

One of the purposes of the invention is that the Gly-Gln within 2 amino acids arising while burning β-endorphin does not have any known adverse effects. Thus, this will be an advantage of Gly-Gln against current therapeutic agents use in depression and/or anxiety disorders which have several side effects mentioned in this text previously.

Another purpose of this invention is that there is not any known adverse effect or toxicological harm of Gly-Gln because it is a molecule present in our body.

In order to achieve the above-mentioned purposes, this invention is related with the use of glycyl-glutamine against depression and anxiety disorders.

The structural and characteristic specifications and all advantages of this invention shall be understood more clearly due to the figures provided in the following and detailed descriptions by making references to these figures,

FIGURES WHICH SHALL HELP UNDERSTANDING THE INVENTION

FIG. 1: It is the graphical view of the impact of centrally administered Gly-Gln injection on the first inaction time.

Figure 2:
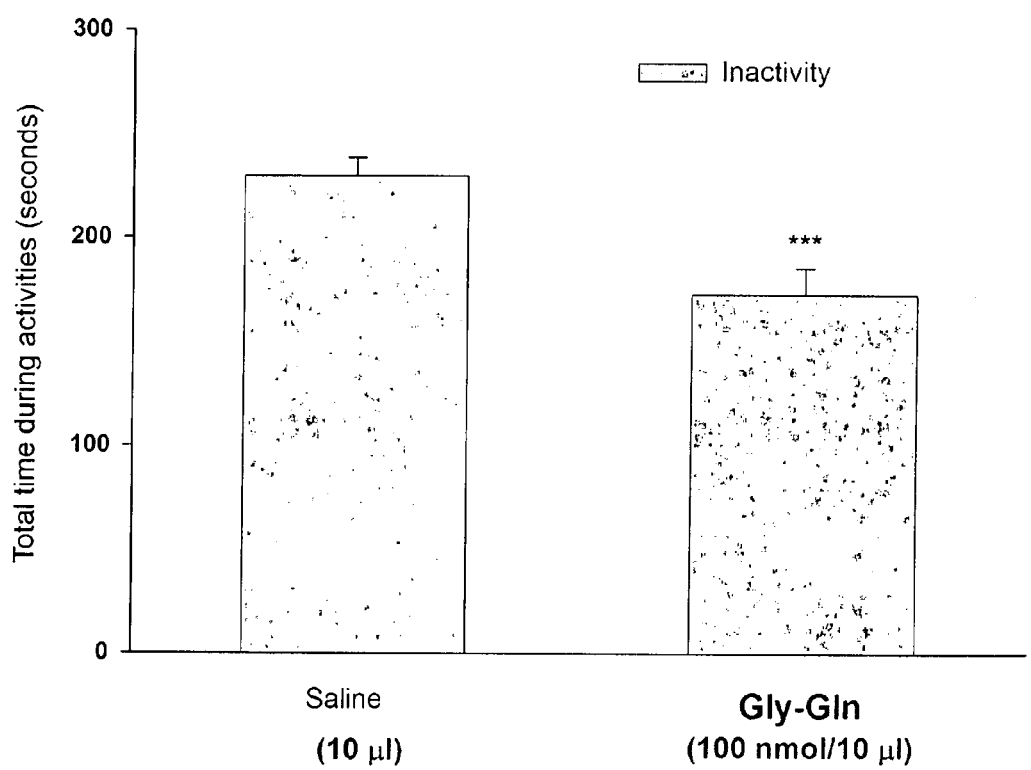

FIG. 2: It is the graphical view of the impact of centrally administered Gly-Gln injection on total inaction time.

Figure 3:
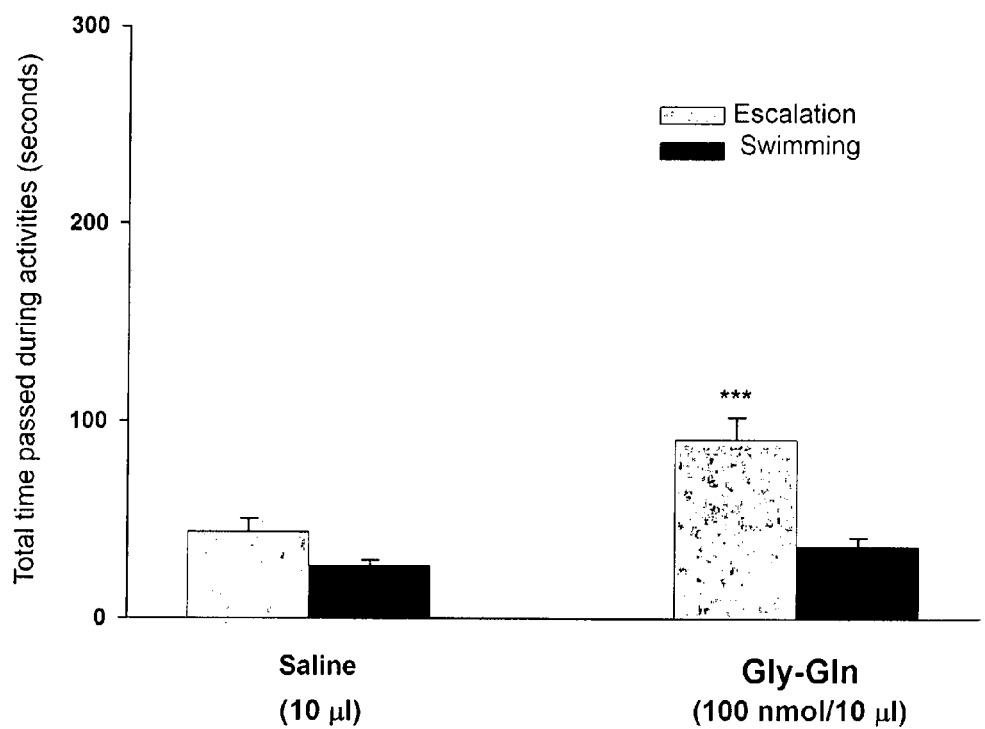

FIG. 3: It is the graphical view of the impact of centrally administered Gly-Gln injection on escalation and flotation time.

Figure 4:
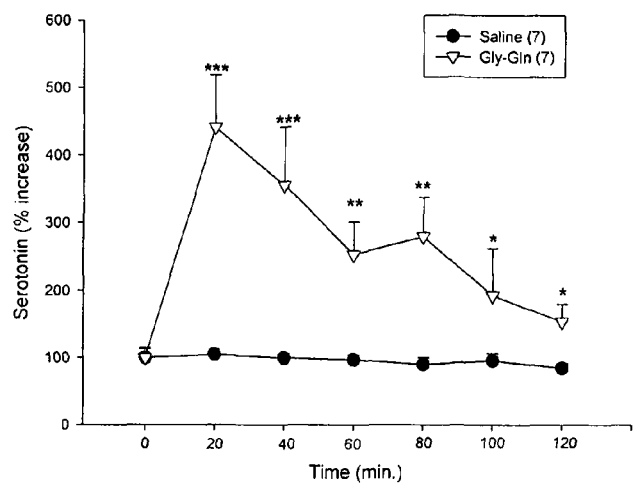
Figure 5:
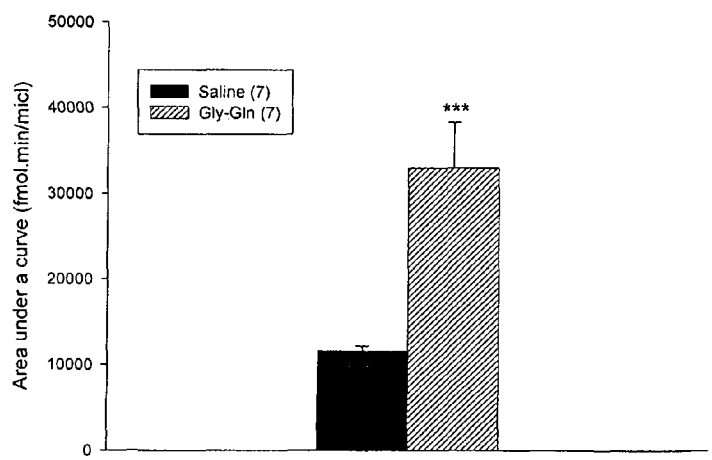

FIGS. 4 and 5: The impact of Gly-Gln on serotonin output of the nucleus accumbency section of the brain following the centrally administered Gly-Gln injection is seen here.

It is not mandatory to scale drawings and sometimes the details, which are not necessary for understanding the invention may be omitted. Furthermore, the same number indicates the elements, which have closely similar in size or at least closely similar in respect of their functions.

DETAILED DESCRIPTION OF THE INVENTION

In this detailed description, the preferred structuring of subject matter glycyl-glutamine while using against depression and anxiety disorder are described solely for making you understand the subject better in a way, which will not establish any restricting effects.

The invention is related with the use of glycyl-glutamine (Gly-Gln) molecule with very little adverse effects and no toxic impacts, which can be synthesized endogenously in our body for treatment of depression and anxiety disorders. In the preferred structuring of the invention, the above-mentioned glycyl-glutamine is used for treatment purposes as 100 nmol/10 μl (100 Nano moles/10 microliters). However, these doses selected for laboratory animals (in this case rats) and have used into the brain directly. Of course the dose will be different in different species and the dose depends the administration route (oral, parenteral and all of other known routes in medicine) of drug. The aim of the drug administration is to achieve minimum therapeutic plasma levels and not to reach minimum toxic consantrion. Thus the dose depends of the patients' age, gender, body weight, liver and kidney functionality and the genetic factors. As a result, the dose of Gly-Gln in the treatment and/or prophylaxis of depression and/or anxiety should be chosen to achieve therapeutic concentration in the plasma.

Additionally, intracerebroventricular route (into the lateral ventricles of brain directly) is a very helpful in experimental models for to show investigators drugs' central effects but it is an unacceptable route for human beings in normal medical conditions. Therefore, Gly-Gln should be use with regular routes in medical applications such as intravenously, intramuscular, intra-arterial, etc. but when administered peripherally Gly-Gln could not across the blood-brain barrier. As a result of that could not generate central effects in the brain. To achieve therapeutic effects against depression and/or anxiety cyclo Gly-Gln, which is a derivative of Gly-Gln, should be use to generate central effects in the brain. Cyclo Gly-Gln could be across blood-brain barrier and generate central effects.

Subject matter glycyl-glutamine (Gly-Gln) comes off while β-endorphin is being burned in the body. Molecules, which are smaller than beta-endorphin, are developed as a result of proteolytic disintegration (Ng et al. 1981). These are beta-endorphin$_{1-26}$, beta-endorphin$_{1-27}$ and Gly-Gln. Antagonization of effects of beta-endorphin by means of beta-endorphin$_{1-27}$ has made us think that Gly-Gln as another breakdown product might show similar effects. In the following studies, it has been shown that Gly-Gln, which has been applied on the brainstem of rodents iontophoretically, had an inhibiting effect on cell ignition and this breakdown product might be a peptide with inhibiting characteristics (Parish et al., 1983). Continuing studies especially focus on POMC and beta-endorphin. It has been indicated that Gly-Gln antagonized the thermogenesis caused by alpha-MSH as one of the breakdown products of POMC (Resch and Millington, 1993) and eliminated the cardiorespiratory depression caused by beta-endorphin (Unal et al., 1997). Similarly, it has been indicated that Gly-Gln and its cyclic form, which can penetrate and pass through blood brain barrier cyclo Gly-Gln eliminated the cardiorespiratory depression caused by beta-endorphin and morphine (Unal et al., 1997). It is very important for the therapeutic potential of Gly-Gln as a dipeptide reproduced from beta-endorphin to eliminate the adverse effects arising after use of morphine without altering its analgesic effects (Owen et al., 2000). The studies performed on use of alcohol can be given as examples for other significant studies by Gly-Gln. It has been found that beta-endorphin administered centrally increased use of alcohol while Gly-Gln decreased such use (Resch et al., 2005; Resch and Simpson, 2008a and 2008b; Simpson et al., 1998). It has been shown in the studies performed by nicotine and morphine, which have additive side effects, that Gly-Gln has prevented the conferment and deprivation symptoms against these materials (Cavun et al., 2005; Goktalay et al., 2006). It has been shown in the studies which have been firstly performed by morphine that Gly-Gln has prevented the conditioned place preference caused by morphine, inhibited addition and tolerance developments and decreased deprivation symptoms (Cavun et al., 2005). In the studies performed by nicotine, it has been found that Gly-Gln has prevented conditioned place preference and deprivation syndrome (Goktalay et al., 2006).

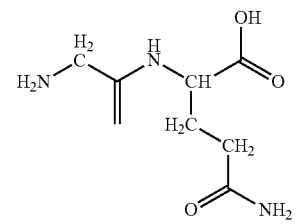

Gly-L-Gln

Chemical composition of Glycyl-glutamine

Subject matter glycly-glutamine is a molecule in our body. Therefore, in terms of adverse effects and toxicological characteristics, it has an edge over other chemicals used in current technique in medical use.

It has been proven as a result of the tests performed on animals that Glycyl-glutamine is therapeutic on depression and anxiety disorders. These aforementioned studies have been performed by means of "the Forced Swimming Test" method, which is the most applied animal model, used in antidepressant treatment surveys. The forced swimming test had been developed by Porsolt et al., (1978) and it is the most applied animal model in depression surveys especially the antidepressant treatment surveys. A rodent or a mouse is placed inside a cylinder tank filled with water and then the time passed until the animal is inactive and how much the animal becomes inactive in a particular period of time are measured. After the same animal is placed in the same tank twenty-four hours after the first time, it is observed that the time passes until inactivity reduces. Inactivity is expressed as losing behaviors of trying to escape in other words "behavioral helplessness". The forced swimming test is a similar response to learned helplessness. The efforts spent for an escape comes to an end for the animal, which understands it is exposed to a stress it will not be able to escape. Thus, it can be understood by that test model whether the antidepressant medications, which are administered before the second administration, show antidepressant effects or not. In practice, the post-treatment behaviors of the animal change for reducing behavioral helplessness. The time passed until inactivity is extended by means of acute or short-term antidepressant treatments and total time of inactivity is decreased. This result is expressed as that the antidepressant medications increase the active coping response of swimming stress (Basar and Ertugrul, 2005). Because, it is an easy to apply practice, this model is used extensively (Cryan et al., 2002).

In FIG. 1, the effect of intracerebroventricular Gly-Gln injection on the first term of inactivity. When, Gly-Gln has been administered centrally, it has extended the time passed until first inactivity compared to the control animals. While, the time passed until first inactivity of the rodents which have been centrally administered saline (10 µl) has been 14.9±2.8 seconds (n=14), the time passed until first inactivity of the rodent which have been applied Gly-Gln (100 nmol/10 µl) by that same way has been increased to 28.1±6.1 seconds (n=12), (p<0.05). This finding shows us that Gly-Gin increases the active coping response of rodents against swimming stress.

In FIG. 2, the effect of intracerebroventricular Gly-Gln injection on the total term of inactivity. When, Gly-Gln has been administered centrally, it has reduced the total time of inactivity compared to the control animals. While, the total inactivity time of the rodents which have been centrally administered saline (10 µl) has been 229.4±8.9 seconds (n=14), the time passed until first inactivity of the rodent which have been applied Gly-Gln (100 nmol/10 µl) by the same way has been increased to 172.5±12.8 seconds (n=12), (p<0.001). This finding shows us that Gly-Gln increases the active coping response of rodents against swimming stress.

In FIG. 3, the effect of intracerebroventricular Gly-Gln injection on the escalation and swimming times. As the control group, the escalation and swimming times of the rodents which have been centrally administered saline (10 µl) have been respectively 43.9±7.0 and 26.7±2.9 seconds, (n=14) These escalation and swimming times for the rodents which have been administered Gly-Gln (100 nmol/10 µl) by the same way have been respectively 90.8±11.4 and 36.8±4.3 seconds (n=12). This findings statistically shows that there is not any statistical difference between the control and medication groups in terms of total time of swimming activities throughout the experiment (p>0.05), while the total escalation activities are more in the medication group (p>0.001). This finding shows us that Gly-Gln increases the active coping response of rodents against swimming stress.

Shortly, statistically significant differences between the rodents, which have been centrally saline, and Gly-Gln have been found. As, it is clearly indicated in the descriptions of the figures, it can be said that Gly-Gln increases active coping response against swimming stress of rodents. This result is important for considering Gly-Gln as a potential antidepressant.

The source of the antidepressant effects of Gly-Gln, which is mentioned in the figure descriptions above, have been analyzed and shown in FIGS. 4 and 5. In FIGS. 4 and 5; the effect of Gly-Gin on the serotonin output at the nucleus accumbency section of the brain upon intracerebroventricular Gly-Gln injection can be seen. As a result of the studies performed by means of brain micro-dialysis, it has been recognized that glycyl-glutamine which is centrally and singly (intracerebroventricular; isv) administered in 100 nmol dose has extremely increased the serotonin output at the nucleus accumbency section of the brain (p<0.001). An increase in serotonin outputs can be observed in all time intervals throughout 2 hours of monitoring period following the Gly-Gln injection; however, no serotonin output could be observed from the rodents in the control group who had been administered saline injections by the same way. Serotonin, which is structurally a monoamine neurotransmitter, is a hormone, which makes people feel happy, energetic and lively. When, the subject matter hormone serotonin is deficient in people, they feel depressive, tired and boring. In this respect, significant increases observed on serotonin levels by means of glycyl-glutamine administrations show that subject matter glycyl-glutamine is effective on ones suffering from depressing and anxiety. Furthermore, the word "Saline" indicated in FIGS. 4 and 5 means salty water. It is used for comparing with the tested medication by administering on the control group.

The non-diluted form of Glycyl-glutamine can be stored in a refrigerator at −20° C. for a very long period of time. After, it is diluted by saline; it can be stored in a refrigerator at +4° C. between 24-48 hours. It can be stored in room temperature for 10-12 hours.

REFERENCES

Baldwin D, Rudge S (1995) The role of serotonin in depression and anxiety. Int Clin Psychopharmacol.,9:41-45.

Basar K, Ertugrul A. (2005) Depresyon Ara?t?rmalar?nda Kullan?lan Hayvan Modelleri. Klinik Psikiyatri,8:123-134

Cavun S, Goktalay, G, Millington WR. (2005) Glycyl-glutamine, an endogenous beta-endorphin-derived peptide, inhibits morphine-induced conditioned place preference, tolerance, dependence, and withdrawal. J Pharmacol Exp Ther., 315(2):949-958.

Cryan JF, Markou A, Lucki I. (2002) Assessing antidepressant activity in rodents: recent developments and future needs. Trends Pharmacol Sci. 2002, 23:238-245.

Goktalay G, Cavun S, Levendusky MC, Hamilton JR, Millington WR. (2006) Glycyl-glutamine inhibits nicotine conditioned place preference and withdrawal. Eur J Pharmacol. ,530(1-2):95-102.

Lesch KP (1991) 5-HT1A receptor responsivity in anxiety disorders and depression. Prog Neuropsychopharmacol Biol Psychiatry, 15:723-733.

Ng TB, Chung D, Li CH. (1981) Isolation and properties of beta-endorphin-(1-27), N alpha-acetyl-beta-endorphin, corticotropin, gamma-lipotropin and neurophysin from equine pituitary glands. Int J Pept Protein Res., 18(5):443-450.

Owen MD, Unal CB, Callahan MF, Trivedi K, York C, Millington WR. (2000) Glycyl-glutamine inhibits the respiratory depression, but not the antinociception, produced by morphine. Am J Physiol Regul Integr Comp Physiol., 279(5):R1944-1948.

Parish DC, Smyth DG, Normanton JR, Wolstencroft JH. (1983) Glycyl glutamine, an inhibitory neuropeptide derived from beta-endorphin. Nature, 306(5940):267-270.

Resch G E, Millington W R. Glycyl-L-glutamine antagonizes alpha-MSH-elicited thermogenesis. Peptides. 1993; 14(5):971-5.

Resch GE (2005), Shridharani S, Millington WR, Garris DR, Simpson CW. (2005) Glycyl-glutamine in nucleus accumbens reduces ethanol intake in alcohol preferring (P) rats. Brain Res., 1058(1-2):73-81.

Resch GE, Simpson CW. (2008) Glycyl-glutamine reduces ethanol intake at three reward sites in P rats. Alcohol., 42(2):99-106.

Resch GE, Simpson CW. (2008) Cyclo-glycyl-glutamine inhibits ethanol intake in P and Sprague-Dawley rats. Peptides, 29(3):430-439.

Simpson CW, Resch GE, Millington WR, Myers RD. (1998) Glycyl-L-glutamine injected centrally suppresses alcohol drinking in P rats. Alcohol., 16(2):101-107.

Stahl SM (2000) Essential Psychopharmacology, New York, Cambridge University Press, p300.

Unal CB, Owen MD, Millington WR. (1997) Cyclo(Gly-Gln) inhibits the cardiorespiratory depression produced by beta-endorphin and morphine. Brain Res. 1997, 747(1):52-59

Zhang Y, Yan H, Lv SG, Wang L, Liang GP, Wan QX, Peng X. (2013) Effects of glycyl-glutamine dipeptide supplementation on myocardial damage and cardiac function in rats after severe burn injury. Int J Clin Exp Pathol., 6(5):821-830.

The invention claimed is:

1. A method of treating depression in a subject in need thereof, the method comprising:
   administering glycyl-glutamine (Gly-Gln) to the subject so as to treat depression in the subject in need thereof.

2. The method of claim 1, wherein said Gly-Gln includes cyclo Gly-Gln.

3. The method of claim 1, wherein the stop of administering is orally or parenterally administering.

4. The method of claim 3, wherein said parenterally administering is intravenously, intramuscularly, intraperitoneally, intradermal or subcutaneously.

5. A method of treating anxiety in a subject in need thereof, the method comprising:
   administering glycyl-glutamine (Gly-Gln) to the subject so as to treat depression in the subject in need thereof.

6. The method of claim 5, wherein said Gly-Gln includes cyclo Gly-Gln.

7. The method of claim 5, wherein the step of administering is orally or parenterally administering.

8. The method of claim 7, wherein the parenterally administering is intravenously, intramuscularly, intraperitoneally, intradermal or subcutaneously.

\* \* \* \* \*